US009242071B2

United States Patent
Morgan et al.

(10) Patent No.: US 9,242,071 B2
(45) Date of Patent: Jan. 26, 2016

(54) CONNECTOR HUB APPARATUS FOR CATHETER AND METHODS OF USE

(71) Applicant: BiO2 Medical, Inc., San Antonio, TX (US)

(72) Inventors: Jeremy Morgan, Idaho Springs, CO (US); Jeffrey N. Steinmetz, Arvada, CO (US)

(73) Assignee: BIO2 MEDICAL, INC., Golden, CO (US)

( * ) Notice: Subject to any disclaimer, the term of this patent is extended or adjusted under 35 U.S.C. 154(b) by 0 days.

(21) Appl. No.: 13/737,694

(22) Filed: Jan. 9, 2013

(65) Prior Publication Data

US 2013/0204206 A1    Aug. 8, 2013

Related U.S. Application Data

(60) Provisional application No. 61/584,716, filed on Jan. 9, 2012.

(51) Int. Cl.
*A61M 39/10*    (2006.01)
*A61M 25/00*    (2006.01)
(Continued)

(52) U.S. Cl.
CPC ....... *A61M 25/0097* (2013.01); *A61M 25/0014* (2013.01); *A61M 39/06* (2013.01); *A61M 39/10* (2013.01); *A61M 39/22* (2013.01); *A61M 2025/0681* (2013.01); *Y10T 29/49826* (2015.01)

(58) Field of Classification Search
CPC ............ A61M 25/00; A61M 25/0014; A61M 25/0097; A61M 39/00; A61M 39/06; A61M 39/0606; A61M 39/0613; A61M 39/0693; A61M 39/10; A61M 39/1011; A61M 2025/00; A61M 2039/00; A61M 2039/06; A61M 2039/10; A61M 2039/062; A61M 2039/0229; A61M 2039/0686; A61M 2025/0681; A61M 39/22; F16L 37/086; F16L 37/098; Y10T 29/49826
USPC ................. 604/246, 247, 533, 534, 535, 537, 604/164.07, 249, 171; 251/149.1; 285/319; 24/614, 615
See application file for complete search history.

(56) References Cited

U.S. PATENT DOCUMENTS 5,324,082 A * 6/1994 McNaughton et al. ......... 285/93
5,911,710 A * 6/1999 Barry et al. .................... 604/249
(Continued)

OTHER PUBLICATIONS

International Search Report issued in corresponding foreign application, PCT/US2013/020855, pp. 1-7 (Apr. 25, 2013).
(Continued)

*Primary Examiner* — Edelmira Bosques
*Assistant Examiner* — Nicholas Meghri
(74) *Attorney, Agent, or Firm* — David G. Rosenbaum; J. Peter Paredes; Rosenbaum IP, P.C.

(57) ABSTRACT

A hub assembly is provided for accommodating a medical professional to grip and manipulate two components of a catheter hub and move one component longitudinally relative to the other, then removably engaging the two components of the catheter hub to restrict movement there between. The two catheter hub components include a proximal hub and a distal hub. The proximal hub and the distal hub are configured to removably engage with one another. The proximal hub is affixed to a first catheter member, such as a multi-lumen catheter, while the distal hub is affixed to a second catheter member, such as a sheath. The first catheter member and the second catheter member are cooperatively engaged and concentric with one another. Relative movement of the proximal and distal hubs translates into relative movement of the first and second catheter members.

15 Claims, 7 Drawing Sheets

(51) Int. Cl.
*A61M 39/22* (2006.01)
*A61M 39/06* (2006.01)
*A61M 25/06* (2006.01)

(56) References Cited

U.S. PATENT DOCUMENTS

| | | | |
|---|---|---|---|
| 7,004,929 B2* | 2/2006 | McWethy et al. | 604/198 |
| 7,806,889 B2 | 10/2010 | Raulerson et al. | 604/523 |
| 8,038,667 B2 | 10/2011 | Racz et al. | 604/533 |
| 2002/0138042 A1* | 9/2002 | Llorach et al. | 604/187 |
| 2006/0135973 A1* | 6/2006 | Hawkins et al. | 606/167 |
| 2007/0088277 A1* | 4/2007 | McGinley et al. | 604/167.01 |
| 2007/0260221 A1 | 11/2007 | Chesnin | 604/523 |
| 2009/0062840 A1 | 3/2009 | Angel | 606/200 |
| 2009/0297260 A1* | 12/2009 | Doll et al. | 403/325 |
| 2010/0204635 A1 | 8/2010 | Haarala et al. | 604/6.16 |
| 2010/0217304 A1 | 8/2010 | Angel et al. | 606/200 |
| 2011/0125097 A1 | 5/2011 | Shaw et al. | 604/164.12 |

OTHER PUBLICATIONS

Written Opinion issued in corresponding foreign application, PCT/US2013/020855, pp. 1-4 (Apr. 25, 2013).

International Preliminary Report on Patentability issued in corresponding foreign application, PCT/US2013/020855, pp. 1-6 (Jul. 24, 2014).

* cited by examiner

CONNECTOR HUB APPARATUS FOR CATHETER AND METHODS OF USE

CROSS-REFERENCE TO RELATED APPLICATIONS

The present application claims priority to U.S. Provisional Ser. No. 61/584,716, filed Jan. 9, 2012, which is incorporated by reference in its entirety.

BACKGROUND

The invention generally relates to hub assemblies for catheters. Catheters require that after deployment of filter, stent, or other similar intravascular medical device, two hubs may be attached to one another to prevent movement relative to one another. The intravascular medical device may, for example, be a vascular or vena cava filter for capturing embolic material in the blood flow, a stent, an embolic filter, an angioplasty balloon, a drug delivery device, or similar such minimally invasive intravascular device.

SUMMARY OF THE INVENTION

A hub assembly is provided for accommodating a medical professional to grip and manipulate two components of a catheter hub and move one component longitudinally relative to the other, then removably engaging the two components of the catheter hub to restrict movement there between. The two catheter hub components include a proximal hub and a distal hub. The proximal hub and the distal hub are configured to removably engage with one another. The proximal hub is affixed to a first catheter member, such as a multi-lumen catheter, while the distal hub is affixed to a second catheter member, such as a sheath. The first catheter member and the second catheter member are cooperatively engaged and concentric with one another. Relative movement of the proximal and distal hubs translates into relative movement of the first and second catheter members. Thus, when the proximal hub is either rotated or longitudinally moved relative to the distal hub, the first catheter member will be rotated or longitudinally moved relative to the second catheter member. It will be understood that the first catheter member may be provided as a carrier for a medical device, such as a vena cava filter, positioned at a distal end of the first catheter member.

The methods, systems, and apparatuses are set forth in part in the description which follows, and in part will be obvious from the description, or can be learned by practice of the methods, apparatuses, and systems. The advantages of the methods, apparatuses, and systems will be realized and attained by means of the elements and combinations particularly pointed out in the appended claims. It is to be understood that both the foregoing general description and the following detailed description are exemplary and explanatory only and are not restrictive of the methods, apparatuses, and systems, as claimed.

BRIEF DESCRIPTION OF THE DRAWINGS

In the accompanying figures, like elements are identified by like reference numerals among the several preferred embodiments.

DETAILED DESCRIPTION OF THE INVENTION

The foregoing and other features and advantages of the invention are apparent from the following detailed description of exemplary embodiments, read in conjunction with the accompanying drawings. The detailed description and drawings are merely illustrative of the invention rather than limiting, the scope of the invention being defined by the appended claims and equivalents thereof In the following description, the terms "distal" and "proximal" are intended to be spatial orientation descriptors relative to the longitudinal axis of the catheter assembly. Thus, a "proximal" side refers to a side of an element generally facing the medical professional and away from the patient and, conversely, a "distal" side refers to a side of an element generally facing away from the medical professional and toward the patient. Likewise a pair of elements described as "proximal" and "distal" elements are understood to have the same spatial relationship as described hereinabove for the sides of an element.

Figure 1A:
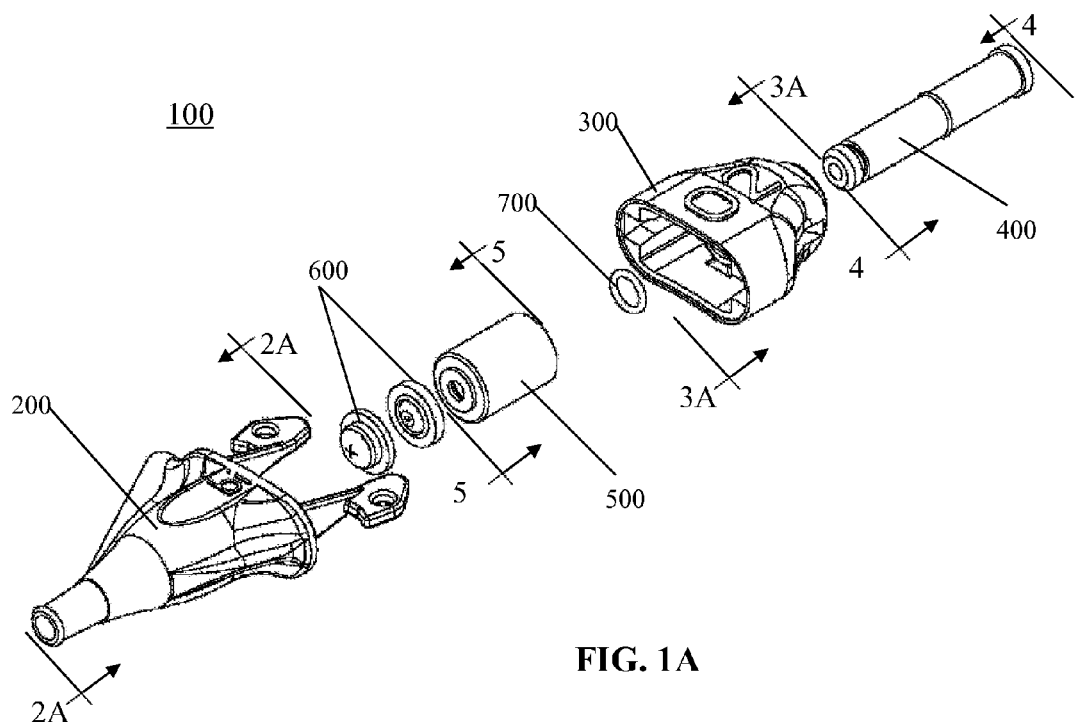
FIG. 1A is a perspective exploded view of the hub assembly in accordance with one embodiment.
Figure 1B:
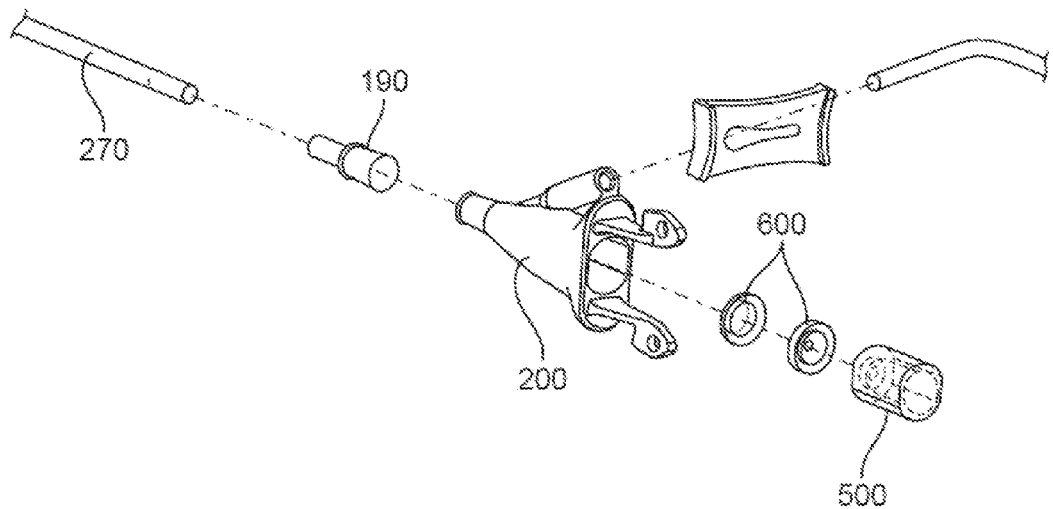
FIG. 1B is a perspective exploded view of a portion of the hub assembly in accordance with an alternative embodiment, including a catheter sheath and a strain relief element.

Generally speaking, the catheter connector hub assembly 100 comprises a proximal hub member 300 removably coupled to a distal hub member 200 generally along a longitudinal axis, as shown in FIG. 1. The proximal hub member 300 couples to a first catheter member 800 (not shown, see FIG. 7A), such as a multi-lumen catheter, as disclosed in commonly assigned U.S. application Ser. Nos. 11/849,225 and 12/684,839, herein incorporated by reference. The distal hub member 200 couples to a second catheter member 270 (not shown, see FIGS. 1B, 7A), such as a catheter sheath. The first catheter member 800 and the second catheter member 270 are cooperatively and concentrically engaged relative to each other, such that movement of either the distal hub member 200 or the proximal hub member 300 translates movement to the respective second catheter member 270 or the first catheter member 800. The second outer catheter member and the first inner catheter member are longitudinally and axially moveable relative to one another. More particularly, the proximal hub limits and/or controls the relative axial movement of the inner catheter relative to the outer catheter and that provides a locked position and kinking resistance for the first inner catheter member during its longitudinal and axial movement relative to the second outer catheter member. In some embodiments, proximal and/or distal hub components are small relative to the larger translation distance between the proximal and distal hub components.

The catheter connector hub assembly 100 further comprises a core member 400, a sealing member 500, a hemostasis valve 600, and an o-ring 700. The core member 400 is principally disposed within the proximal hub member 300, and the sealing member 500 and the hemostasis valve 600 are disposed within the distal hub member 200. The catheter connector hub assembly 100 may further comprise a heat shrink strain relief 190, shown in FIG. 1B, disposed about and extending beyond the distal end of the distal hub member 200. The heat shrink strain relief 190 may extend over the coupling of the second catheter member 270 to the distal hub member 200. The heat shrink strain relief provides a mechanical retaining feature between the second catheter member 270 and the distal hub member 200. When heated, heat shrink strain relief 190 shrinks to conform to the size and shape of the underlying material to provide insulation, strain relief, and protection against mechanical damage and abrasion. An adhesive lining may be coupled that melts and flows with the heat shrink strain relief 190, creating a moisture-resistant protective barrier.

Figure 2A:
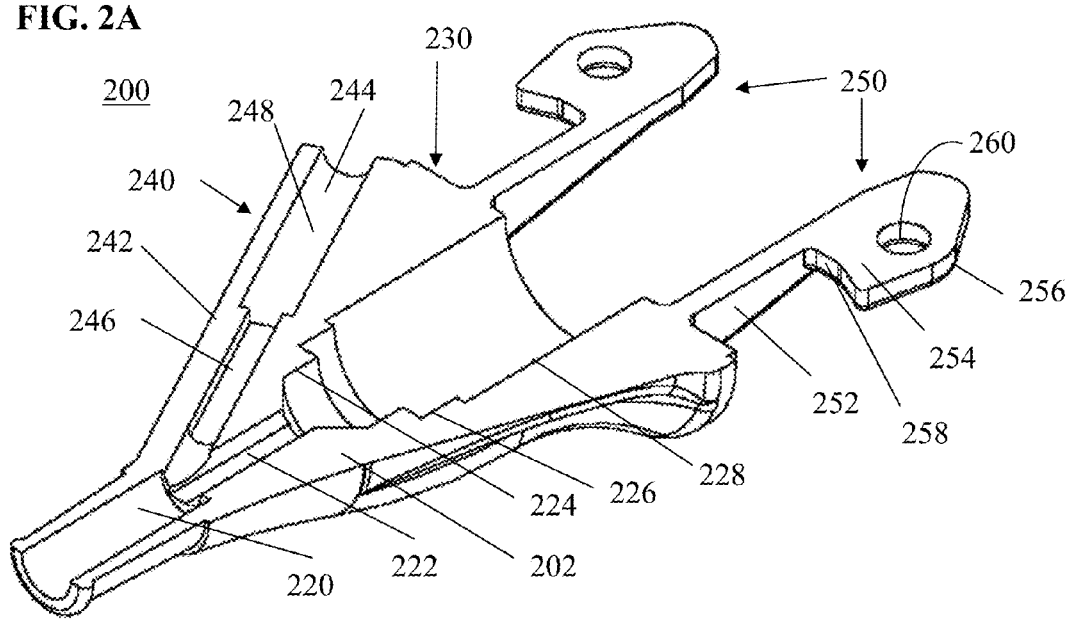
FIG. 2A is a perspective cross-sectional view taken along line 2A-2A of FIG. 1A.

FIG. 2A depicts a cross-sectional view of the distal hub member 200 shown in FIG. 1. The distal hub member 200 comprises a body member 202 having an inside surface defining a longitudinal lumen 220 traversing the longitudinal axis of the distal hub member 200. The longitudinal lumen 220 is heterodiametered, having a first diameter for a distal section 222 of the longitudinal lumen 220, a first expanded section 224 having a diameter greater than the distal section 222, a second expanded section 226 having a diameter greater than the first expanded section 224, and a third expanded section 228 having a diameter greater than the second expanded section 226. The term "heterodiametered" is intended to mean an opening, bore, lumen or channel having regions of differential diameter. This term is intended to include both step-wise changes in diameter, such as that present where a seat or flange is present in the opening, bore, lumen or channel, or tapers where there is a constant change in diameter over a longitudinal region of the opening, bore, lumen or channel.

The distal hub member 200 further comprises a proximal hub attachment member. The proximal hub attachment member of the present embodiment comprises a pair of laterally spaced resilient projections 250. Each resilient projection 250 comprises a proximally-extending arm 252 projecting from a proximal surface 230 of the distal hub member 200. Each of the proximally extending arms 252 may have a planar surface that is orthogonal to a general plane of the distal hub member and tapers proximally away from the proximal surface 230. The reduced mass of material lends resilience to the projection 250 such that it is capable of deflection toward and away from the central longitudinal axis of the catheter hub assembly 100. The resilient projections 250 each further comprise a tab 254 attached to a proximal end of the proximally-extending arm 252, the tab 254 having a generally rounded outside edge including a rounded corner 256. The tab 254 extends generally perpendicular to the axis of the resilient projection 250, proximally and radially outward away the longitudinal axis of the distal hub member 200. Furthermore, the tab 254 includes an interfacing surface 258 that is generally flat and distal-facing.

The proximally-extending arms 252 are fabricated from resilient material such that the proximally-extending arms 252 can deflect radially inwards and return to their non-deflected orientation without plastic deformation. In one embodiment, the resilient material is a polymer material or a metal based material.

The resilient projection 250 may further include an aperture 260 through the tab 254. The aperture 260 is located generally towards the proximal, radially outside section of the tab 254. Aperture 260 is preferably used in practice as a suture aperture in order to secure hub assembly 100 to the patient.

The distal hub member 200 further comprises a side port 240 comprising a tubular member 242 defining a side-branching lumen 244. The side-branching lumen 244 is in fluid communication with the longitudinal lumen 220. The side-branching lumen 244 is heterodiametered, having a distal lumen section 246 with a diameter less than the diameter of a proximal lumen section 248. In the present embodiment, the side-branching lumen 240 is coplanar with the resilient projection 250. In an alternative embodiment, the side-branching lumen 240 may be non-coplanar with the resilient projections 250.

Figure 2B:
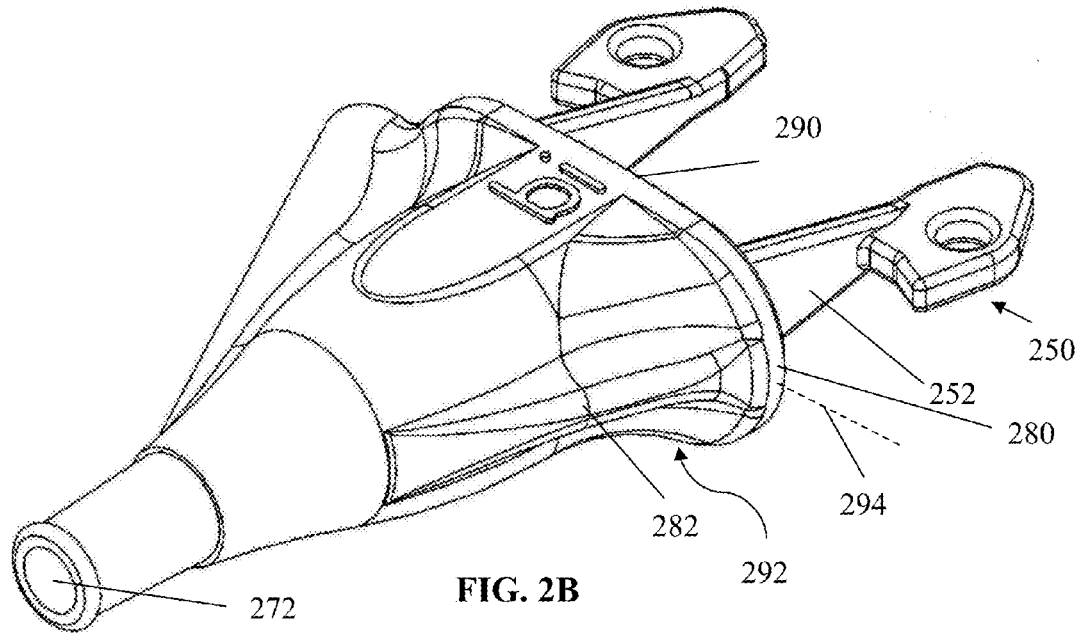
FIG. 2B is a perspective view of a distal hub member of the hub assembly.

The distal hub member 200 further comprises a flange member 280 defining the proximal surface 230 of the distal hub member 200, as shown in FIG. 2B. In the present embodiment, the proximally-extending arms 252 attach to the flange member 280, thereby connecting the resilient projections 250 to the distal hub member 200. In alternative embodiments, the resilient projections 250 may connect to the distal hub member 200 without the flange member 280. The flange member 280 is supported by ribs 282. The ribs 282 taper outward from the body member 202 to the outside edge of the flange member 280. In the present embodiment, one of the ribs 282 is coplanar with and bounded by the side-branching lumen 240. The ribs 282 may optionally be integrally formed with either of the body member 202 or the flange member 280, or both.

Figure 7A:
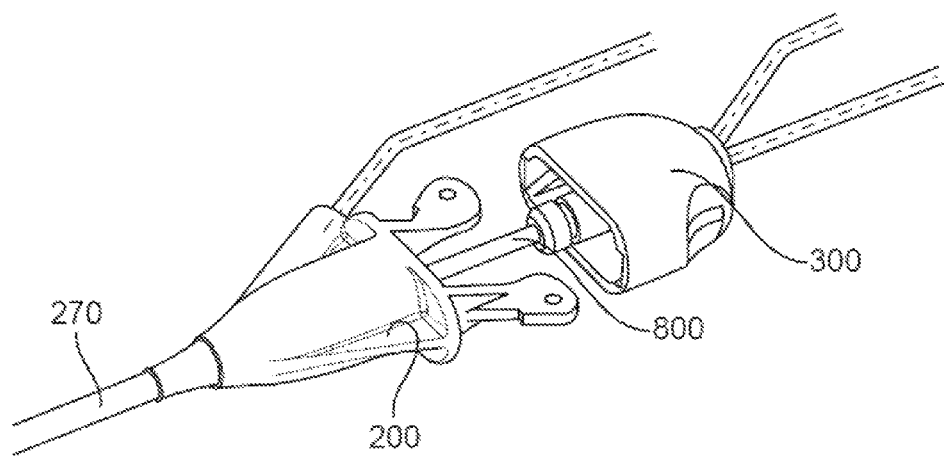
FIG. 7A is a perspective view of the hub assembly coupled to a catheter.
Figure 7B:
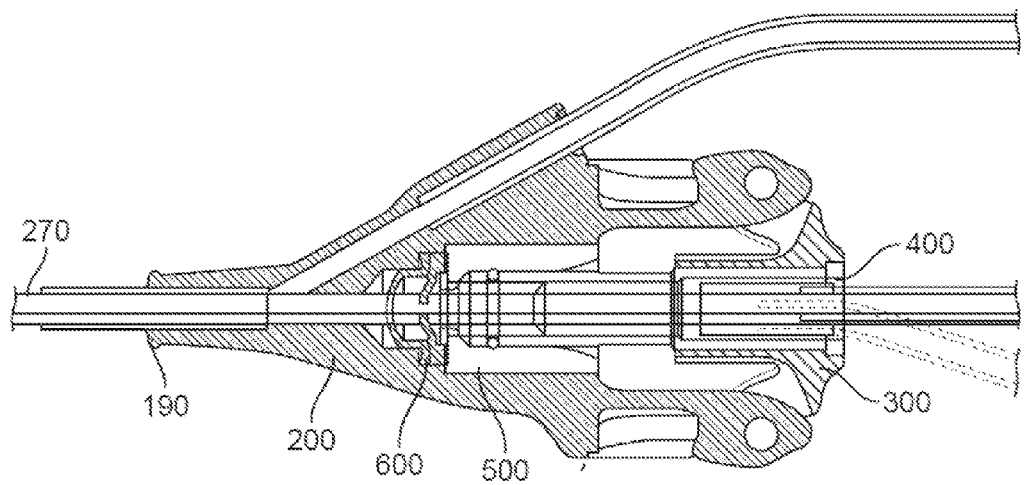
FIG. 7B is a cross-sectional view of the hub assembly of FIG. 7A, wherein the proximal and distal hub members are removably coupled, as well as a strain relief element.

The distal hub member 200 further comprises an outer sheath 270, as shown in FIGS. 1B and 7A-B), extending generally distally form a distal portal 272 of the distal hub member 200. The outer sheath 270 is attached to the distal hub member 200 in the distal section 222 of the longitudinal lumen 220. The outer sheath 270 can be attached by any method that prevents detachment of the outer sheath 270 due to distal forces applied to the outer sheath 270, including the use of adhesives. Alternatively, the outer sheath 270 may be integrally formed with the body member 202 of the distal hub member 200. In some embodiments, a heat shrink strain relief 190 may be disposed over the connection between the outer sheath 270 and the distal hub member 200. In still further embodiments, the outer sheath 270 may comprise a multi-lumen sheath, such as that disclosed in U.S. Provisional Patent Application Ser. No. 61/668,308, filed Jul. 5, 2012, which is hereby incorporated by reference in its entirety.

The distal hub member 200 further comprises an upper surface 290 and a lower surface 292 that each define a contour about a horizontal axis 294 of the distal hub member 200. The contour of the upper surface 290 may be asymmetric to the contour of the lower surface 292 about the horizontal axis 294. Alternatively, the contour of the upper surface 290 may be symmetric about the horizontal axis 294 to the contour of the lower surface 292.

Figure 3A:
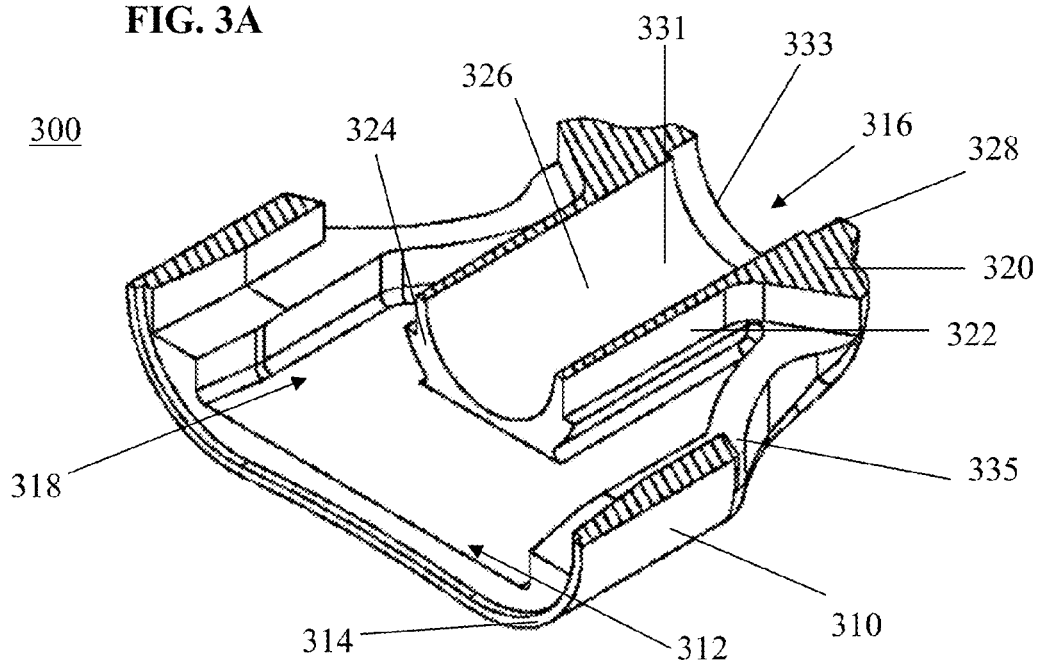
FIG. 3A is a perspective cross-sectional view taken along line 3A-3A of FIG. 1A.

FIG. 3A depicts a cross-sectional view of the proximal hub member 300 shown in FIG. 1. The proximal hub member 300 comprises an outer wall 310 defining an interior cavity 318. The distal end 312 of the proximal hub member 300 is open and is defined by a distal surface 314 of the outer wall 310. The outer wall 310 has a major diameter less than the distance between the radially outside surfaces of the tabs 254 of the resilient projections 250. The interior cavity 318 has a volume sufficient to accommodate the disposal of the resilient projections 250 therein.

The proximal hub member 300 further comprises a central mounting section 320. The central mounting section 320 defines an opening in the proximal end of the outer wall 310, creating a proximal port 316. The proximal port 316 is configured to engage with the core member 400. The central mounting section 320 comprises a distally-extending wall 322 having a distal surface 324 and defining a longitudinal lumen 326. The distally-extending wall 322 further comprises an annular shelf 328 within the longitudinal lumen 326 having a generally flat proximal-facing surface, creating a distal lumen section 331 having a first diameter and a proximal lumen section 333 having a second diameter. In a preferred embodiment, the diameter of the proximal lumen section 333 is greater than the diameter of the distal lumen section 331.

Figure 3B:
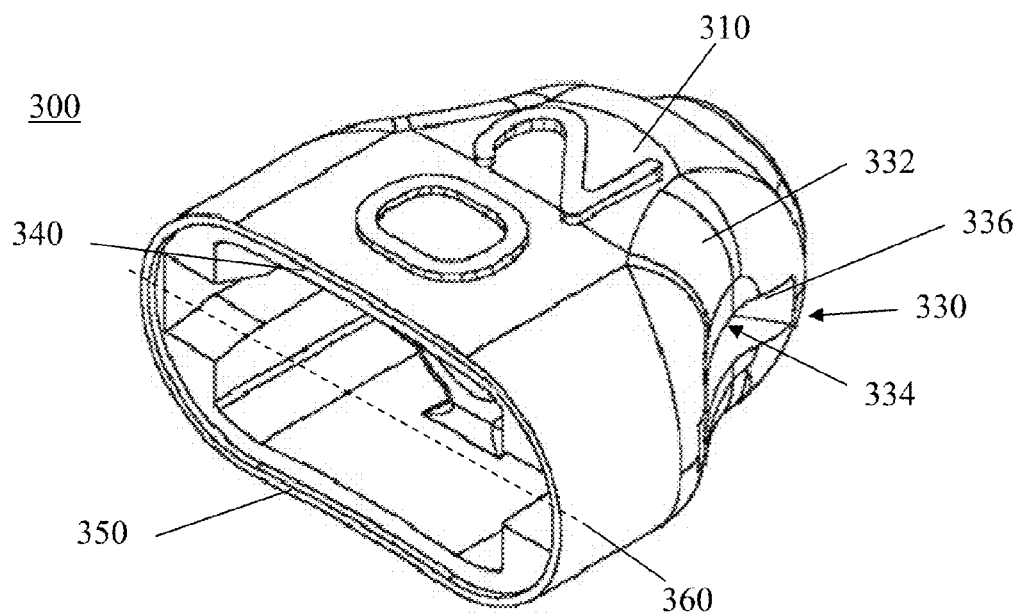
FIG. 3B is a perspective view of a proximal hub member of the hub assembly.

FIG. 3B depicts the proximal hub member 300 as shown in FIG. 1. The proximal hub member 300 further includes a catch opening 330 formed in the outer wall 310. The catch opening 330 is configured to receive the resilient projections 250 therethrough, thereby permitting the removable coupling of the proximal hub member 300 and the distal hub member 200. In the present embodiment, the catch opening 330 comprises a recess 332 in the outer wall 310. The recess 332 is concave, in contrast to the generally convex curvature of the outer wall 310, and it is generally circular, and accommodates a user's fingers to permit depression of the tab 254 of the resilient projection 250 within the recess 332 to disengage the proximal hub member 300 from the distal hub member 200. Within the boundary of the depression 332 is an aperture 334 through the outer wall 310, creating an open area communicating between the interior cavity 318 and the outside environment. The aperture 334 is geometrically configured to follow the curvature of the recess 332 and defines a distal interfacing surface 335, as shown in FIG. 3A. The aperture 334, which in this embodiment is externally configured as a slot, is further dimensioned to allow the tab 254 of the resilient projection clip 250 to pass there through and engage in an abutting and locking fashion to secure the proximal hub member 300 with the distal hub member 200 as illustrated in FIG. 7B. Finally, the aperture 334 defines a proximal surface 336. Alternatively, the proximal hub member 300 may be lockingly engaged with the distal hub member via a fastener, an adhesive, a press fit, a snap fit, a removable attachment, a rotatable attachment, a magnetic attachment, a slidable attachment, ratchet arrangement, or via any method of attachment.

The proximal hub member 300 further comprises an upper surface 340 and a lower surface 350 that each defines a contour about a horizontal axis 360 of the proximal hub member 300. The contour of the upper surface 340 may be asymmetric about the horizontal axis 360 to the contour of the lower surface 350. Alternatively, the contour of the upper surface 340 may be symmetric to the contour of the lower surface 350 about the horizontal axis 360. In either case, the contour of the upper surface 340 should align with the contour of the upper surface 290 of the distal hub member 200 and the contour of the lower surface 350 should align with the contour of the lower surface 292 of the distal hub member 200.

Figure 4:
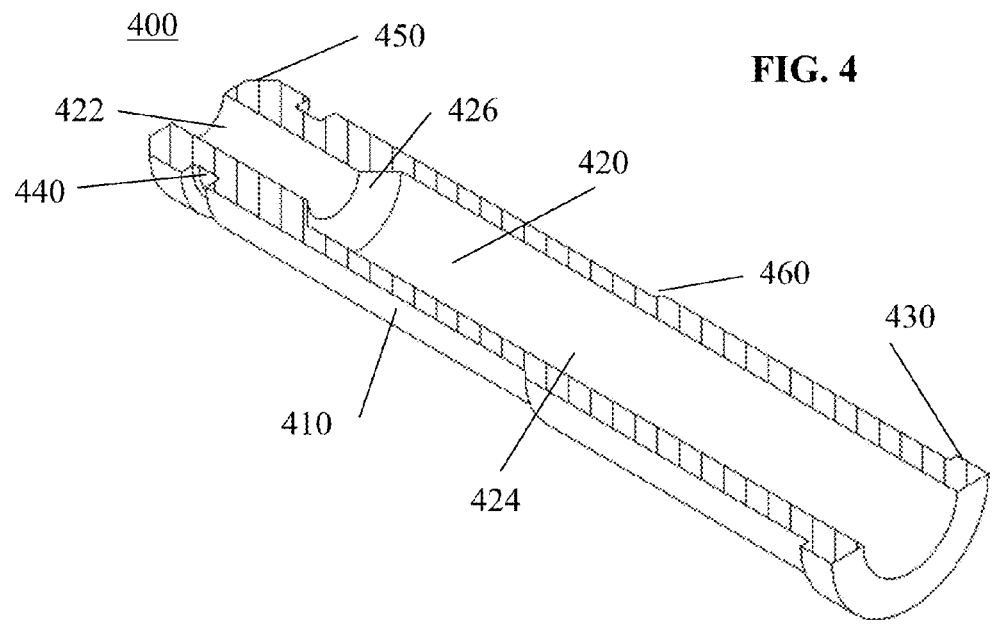
FIG. 4 is a cross-sectional view of the core member taken along line 4-4 of FIG. 1A.

FIG. 4 depicts a cross-sectional view of the core member 400 shown in FIG. 1. The core member 400 is a plug disposed through the opening 316 in the proximal end of the central mounting section 320, through the interior cavity 318, and extending out the distal end 312 of the proximal hub member 300. The core member 400 comprises a wall 410 defining a longitudinal lumen 420, a radially-extending flange 430 at a proximal end of the core member 400, and an annular recess 440 formed in an outside surface of the wall 410. The core member 400 may further comprise a first annular taper 450 formed at the distal end of the core member 400 and a second annular taper 460 intermediate the annular recess 440 and the radially-extending flange 430.

The wall 410 of the core member 400 has an outside diameter that is less than the diameter of the longitudinal lumen 326 of the central mounting section 320, thereby permitting the distal end of the core member 400 to pass therethrough. The radially-extending flange 430 has an outside diameter greater than the diameter of the distal lumen section 331 but less than the proximal lumen section 333, thereby allowing the radially-extending flange 430 to pass through or fit within the proximal lumen section 333 but not the distal lumen section 331. The radially-extending flange 430 engages with the annular shelf 328, thereby preventing the core member 400 from further distal translation with respect to the proximal hub member 300. Furthermore, the core member 400 may optionally be fixed to the proximal hub member 300 by use of an adhesive at any interface between the core member 400 and the central mounting section 320, in particular the annular shelf 328 and the proximal lumen section 333. The adhesive can be used on the surface of the distal lumen section 331.

The longitudinal lumen 420 of the core member 400 comprises a distal narrowed section 422, a proximal widened section 424, and an intermediate tapered section 426 therebetween. The diameter of the distal narrowed section 422 is smaller than the diameter of the proximal widened section 424.

The annular recess 440 is formed in the outer surface of the wall 410 of the core member 400 in a section of the wall 410 that, when the core member 400 is disposed through the central mounting section 320, projects beyond the distal end 312 of the proximal hub member 300. The annular recess 440 serves to seat a seal, such as an O-ring seal 700 (not shown, but shown in FIG. 1), to create a fluid tight seal.

Figure 5:
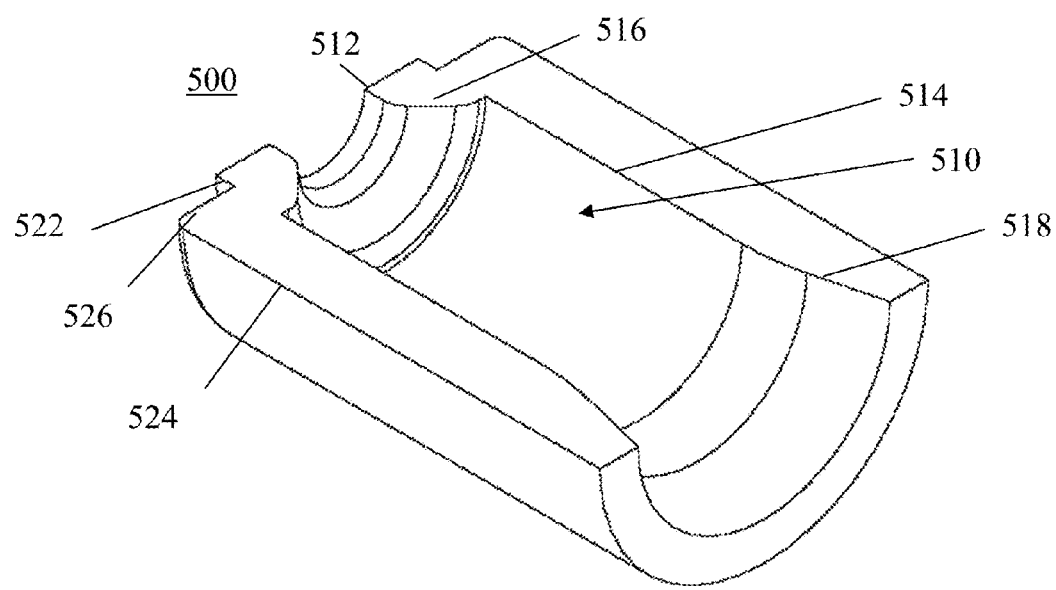
FIG. 5 is a cross-sectional view of the sealing member taken along line 5-5 of FIG. 1A.

FIG. 5 depicts a cross-sectional view of the sealing member 500 shown in FIG. 1. The sealing member 500 is a component configured to be disposed within the longitudinal lumen 220 of the distal hub member 200. The sealing member 500 may be a generally cylindrical member defining a longitudinal lumen 510 having a narrow distal section 512, a wide proximal section 514, a tapering intermediate section 516, and a tapering proximal section 518. Alternatively, the sealing member 500 may be a polygonal shape or interface that mates with and is complimentary to the longitudinal lumen 220. The sealing member 500 further comprises an outside surface having a narrow distal section 522, a wide proximal section 524, and an annular shelf 526 connecting the two. The narrow distal section 522 has a diameter smaller than the diameter of the wide proximal section 524. The wide outer proximal section 524 attaches to the wall surface of the longitudinal lumen 220 of the distal hub member 200 at the third expanded section 228 by any suitable method preventing its movement during normal use, such as by press fit or adhesive. A fluid barrier may thereby be created between the internal cavities/lumens 318 and 220 of the proximal hub member 300 and the distal hub member 200, respectively.

In some embodiments, as shown in FIG. 1B, the generally cylindrical sealing member 500 may have at least one flat edge. The third expanded section 228 of the distal hub member 200 may have a corresponding flat edge configured to align with the flat edge of the sealing member 500, so as to prevent rotation of the sealing member 500 once inserted into the expanded section 228.

The wide inner proximal section 514 of the longitudinal lumen 510 has a diameter that is slightly greater than the outside diameter of the wall 410 of the core member 400, thereby permitting the distal end of the core member 400 to enter the wide inner proximal section 514. Furthermore, the first annular taper 450 of the core member 400 cooperates with the tapering proximal section 518 in facilitating the entry of the distal end of the core member 400 by permitting the core member 400 to enter the wide proximal section 514 off-centered, with the first annular taper 450 interfacing with and sliding along the tapering proximal section 518, thereby centering the core member 400 within the longitudinal lumen 510.

Figure 6:
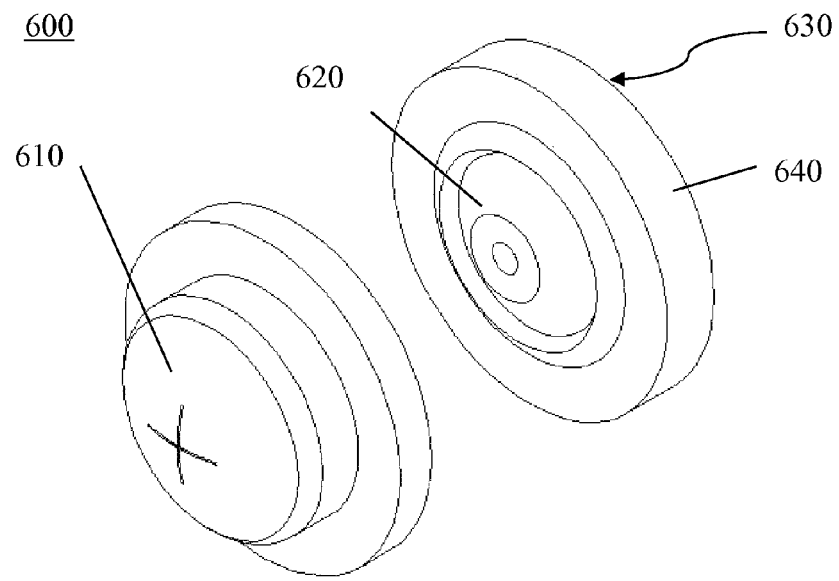
FIG. 6 is a perspective exploded view of a hemostasis valve.

FIG. 6 depicts a hemostasis valve 600 as shown in FIG. 1. The hemostasis valve 600 prevents fluid flow along a passageway formed along its longitudinal axis, which is coaxial with the longitudinal axis of the sealing member 500. In the present embodiment, the hemostasis valve 600 comprises a distal valve member 610 and a proximal valve member 620. The proximal valve member 620 defines a proximal surface 630 and a radially outside surface 640.

The hemostasis valve 600 is disposed distal the sealing member 500 within the distal hub member 200. The proximal surface 630 interfaces with the annular shelf 526 of the sealing member 500, preventing fluid flow around the outside surface 520 of the sealing member 500. The radially outside surface 640 attaches to the surface of the longitudinal lumen 510 at the second expanded section 226 by any suitable method preventing its movement during normal use and forming a fluid seal, such as by press fit or adhesive. Furthermore, the distal valve member 610 interfaces with surface of the longitudinal lumen 220 of the distal hub member 200 at the first expanded section 224, preventing fluid flow therethrough.

Referring to FIG. 1, the o-ring 700 is an annular ring configured to seat within the annular recess 440 of the core member 400. The o-ring 700 extends radially outward from the outside surface of the wall 410. When the core member 400 is disposed within the sealing member 500, the o-ring 700 interfaces with the surface of the longitudinal lumen 510 of the sealing member 500, creating a fluid barrier.

In operation, as illustrated in FIGS. 7A-B, hemostasis valve 600 is first disposed within the distal hub member 200 and attached as described hereinabove. Second, the sealing member 500 is disposed within the distal hub member 200 and is attached as described hereinabove. Third, the core member 400 has a catheter 800 disposed through the longitudinal lumen 420 such that the catheter 800 extends beyond the distal end of the core member 400.

The catheter 800 may optionally be fixed to the core member 400. One method of fixation is to fill the proximal widened section 424 of the core member 400 with a resin that, when cured, adheres to the catheter 800 and the surface of the longitudinal lumen 420. The resin may be cured by any known method, including electromagnetic radiation and heat. In one embodiment, the resin is cured by UV radiation. In that embodiment, the core member 400 is comprised of a UV-transparent material, permitting the UV radiation to pass therethrough. Alternatively, the core member 400 is inserted into the proximal hub member 300.

The core member 400 may be inserted into the proximal hub member 300, such that the distal end of the core member 400 is inserted through the proximal port 316 of the proximal hub member 300. The core member 400 may thus be disposed within the central mounting section 320 of the proximal hub member 300.

A distal end of the catheter 800 is passed through the longitudinal lumens of the proximal hub member 300, the sealing member 500, and the distal hub member 200 as well as the passageway of the hemostasis valve 600, extending beyond the distal end of the distal hub member 200 and into the second catheter member 270, such as an outer catheter sheath, as depicted in FIGS. 7A-B. The distal hub member 200 and the proximal hub member 300 are then moved towards each other. The rounded corner 256 of the tab 254 engages with the distal surface 314 of the wall 310 of the proximal hub member 300, and as the distal hub member 200 translates proximally with respect to the proximal hub member 300, the resilient projections 250 deflect radially inward, permitting the distal hub member 200 to translate further proximally.

As the hub members are pushed closer together, the core member 400 enters the longitudinal lumen 510 of the sealing member 500 as described above. As the core member 400 extends further into the longitudinal lumen 510, the o-ring 700 interfaces with the surface of the longitudinal lumen 510, creating a fluid barrier.

As the distal hub member 200 continues to translate proximally, the tabs 254 of the resilient projections 250 will enter the apertures 334 of the catches 330. When the tabs 254 extend completely through the apertures 334, the resilient projections 250 will be in their un-deflected state. In this state, the proximal surface 336 of the apertures 334 engages with the resilient projections 250, thereby preventing further proximal translation of the resilient projections 250 and the distal hub member 200. Furthermore, in this state, the interfacing surface 258 of the resilient projections 250 interfaces with the distal interfacing surface 335 thereby preventing the distal hub member 200 from translating distally relative to the proximal hub member 300. Therefore, when the resilient projections 250 engage with the catches 330, the distal hub member 200 and the proximal hub member 300 are prevented from translating longitudinally with respect to each other, creating a removable coupling of the two hub members.

To disengage the resilient projections 250 from the catches 330, the user may press the tabs 254 inward, deflecting the resilient projections 250 inward and removing the interface between interfacing surface 258 of the distal hub member 200 and the distal interfacing surface 335 of the proximal hub member 300. Once the resilient projections 250 have been deflected radially inward sufficiently, they will no longer protrude through the apertures 334, thereby decoupling the distal hub member 200 from the proximal hub member 300 and allowing the distal hub member 200 to translate distally relative to the proximal hub member 300. As the distal hub member 200 translates distally, o-ring 700 will cease to interface with the surface of the longitudinal lumen 510 of the sealing member 500 and the core member 400 will translate proximally out of the longitudinal lumen 510. Eventually, the resilient projections 250 will translate distally out of the interior cavity 318 of the proximal hub member 300 through the opening in the distal end 312.

Figure 8:
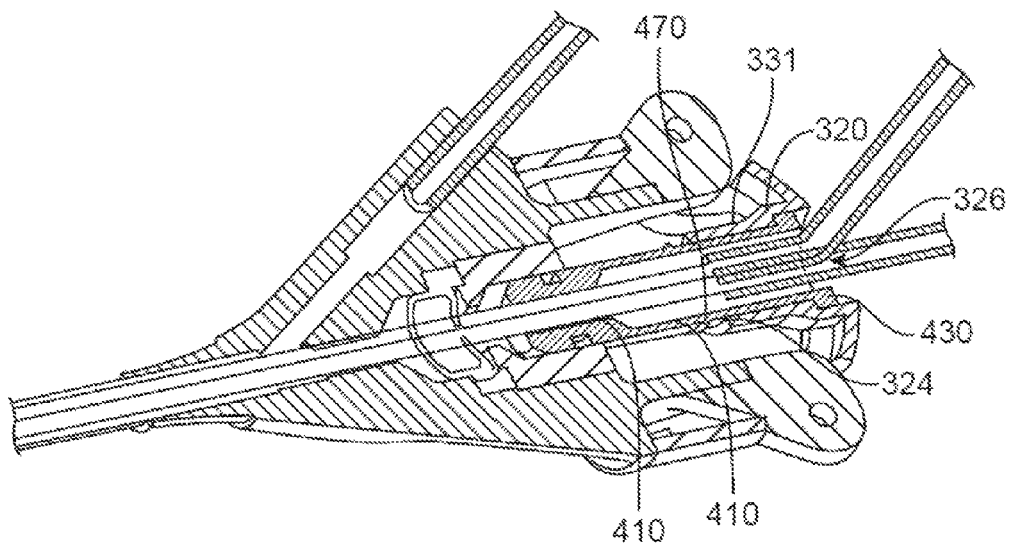
FIG. 8 is a perspective transverse cross-sectional view of the inventive hub assembly illustrating coupling of fluid conduits to the hub assembly, in an alternative embodiment of the core member.

In an alternative embodiment, the core member 400 may further comprise an annular detent 470, as depicted in FIG. 8. The annular detent 470 protrudes radially outward from the outside surface of the wall 410. The annular detent 470 is spaced longitudinally apart from the radially-extending flange 430 a distance greater than the length of the distal lumen section 331, such that when the radially-extending flange 430 engages with the annular shelf 328, the annular detent 470 is disposed distally beyond the distal surface 324 of the central mounting section 320.

The annular detent 470 has an outside diameter greater than the diameter of the longitudinal lumen 326 of the central mounting section 320. To translate through the longitudinal lumen 326, the wall 410 and the annular detent 470 are made of a material with sufficient flexibility to deflect radially inward, thereby reducing the outside diameter of the annular detent 470 to less than the diameter of the longitudinal lumen 326. Once the annular detent 470 is distal the distal surface 324, if the core member 400 begins to translate proximally with respect to the proximal hub member 300, the annular detent 470 engages with the distal surface 324, preventing further proximal translation. As such, longitudinal translation of the core member 400 with respect to the proximal hub member 300 is constrained by the annular detent 470 and the radially-extending flange 430.

Figure 9:
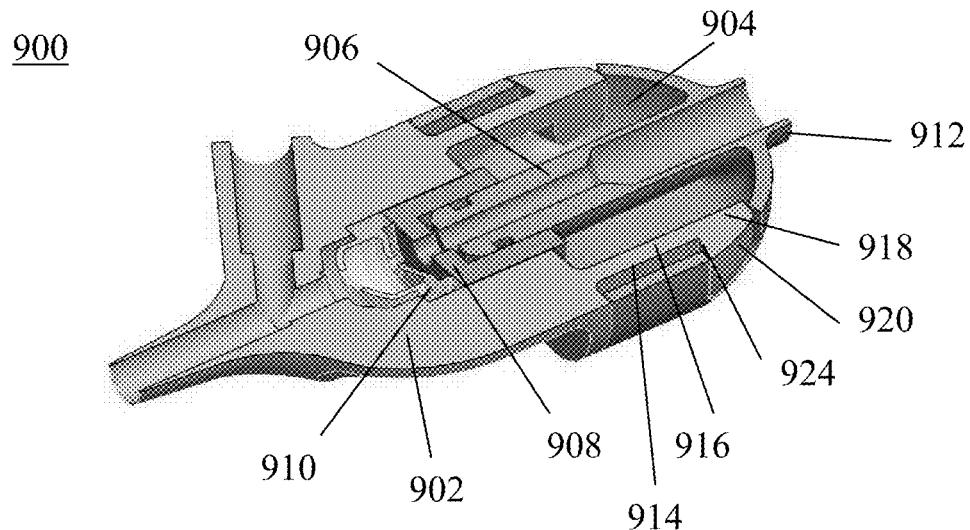
FIG. 9 is a transverse cross-sectional view of an alternative embodiment of the hub assembly.

In a further embodiment, depicted in FIG. 9, a catheter connector hub 900 substantially comprises a distal hub member 902, a proximal hub member 904, a core member 906, a sealing member 908, a hemostasis valve 910, and an o-ring (not pictured), analogous to these elements as presented above in relation to FIGS. 1-8. However, the proximal hub member 904 and the core member 906 are integrally formed as a single piece. Accordingly, the central mounting section is not present in this embodiment. Furthermore, the proximal hub member 904 may include a catheter support wall 912 extending proximally from the proximal end of the proximal hub member 904.

Yet further in this embodiment, the distal hub member 902 may comprise attachment clips 914 that differ from the resilient projections 250 presented above. For instance, the attachment clips 914 include proximally-extending arms 916, but do not include tabs. Instead, the attachment clips 914 include clip heads 918 having a rounded edge 920 and a distal interfacing surface 924 to interact with the proximal hub member 904 substantially as presented above.

Figure 10:
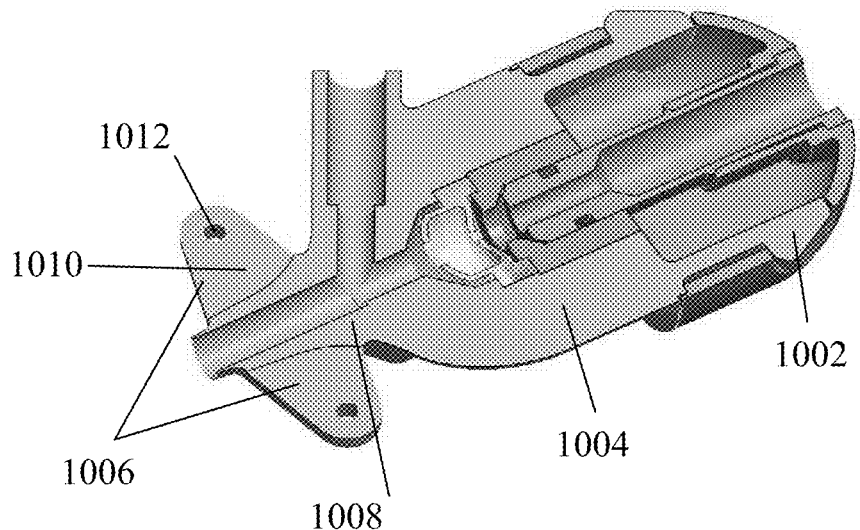
FIG. 10 is a transverse cross-sectional view of an alternative embodiment of the hub assembly.

In a yet further embodiment, as depicted in FIG. 10, a catheter connector hub assembly 1000 is substantially similar to the catheter connector hub as depicted in FIG. 8, with the exception that it includes attachment clips 1002 as presented by the embodiment depicted in FIG. 9. However, the distal hub member 1004 of the present embodiment comprises two suture wings 1006 attached to a distal section of the body member 1008 of the distal hub member 1004. The suture wings 1006 each comprise a tab 1010 that is generally flat and extends radially outward from the longitudinal axis of the distal hub member 1004, and an aperture 1012 formed through the tab. The aperture 1012 may be formed at any place in the tab 1010, such as a radially outward section of the tab 1010 as shown.

Generally, the catheter hub apparatus comprises a distal hub member comprising a longitudinal lumen, having a distal section, a first expanded section, a second expanded section, and a third expanded section, wherein the distal section has a diameter less than the diameter of the first expanded section, the first expanded section has a diameter less than the diameter of the second expanded section, and the second expanded section has a diameter less than the diameter of the third expanded section; a radially-extending flange disposed at a proximal end of the body member; a proximal hub attachment member comprising a proximally-extending arm and a resilient projection, the resilient projection being biased radially outward and having a radially-extending tab with an aperture therethrough; a side port in fluid communication with the longitudinal lumen; and an outer sheath extending distally from the distal end of the longitudinal lumen; a proximal hub member comprising an outer wall defining an internal cavity and having an open distal end, a central mounting section comprising a distally-extending annular wall defining a longitudinal lumen, an annular shelf, and an opening at the proximal end of the proximal hub member, and a catch formed in the outer wall of the body member comprising an aperture formed in the outer wall having a distal interfacing surface; a core member comprising a wall defining a longitudinal lumen having a distal section and a proximal section, wherein the distal section has a diameter less than the diameter of the proximal section, the wall being made of UV-transparent material, a flange at a proximal end of the core member, an annular detent, an annular recess, and UV-curable resin disposed within the proximal section of the longitudinal lumen that has been cured by application of UV radiation; a sealing member attached to an inside surface of the body member of the distal hub member comprising a wall defining a longitudinal lumen, the longitudinal lumen having a diameter greater than an outside diameter of the core member; a hemostasis valve interfaced with the inside surface of the body member of the distal hub member; and an o-ring seated within the annular recess of the core member and interfacing with an inside surface of the sealing member; wherein the resilient projection engages with the catch to couple removably the distal hub member to the proximal hub member, the hemostasis valve forms a fluid barrier preventing proximal fluid flow between a distal end of the longitudinal lumen of the distal hub member and a distal end of the sealing member, and the o-ring forms a fluid barrier between the distal end of the longitudinal lumen of the sealing member and the internal cavity of the proximal hub member.

A catheter hub apparatus comprises a distal hub member having an upper surface defining a contour, a lower surface defining a contour, and a horizontal axis; and a proximal hub member having an upper surface defining a contour, a lower surface defining a contour, and a horizontal axis; wherein the distal hub member upper contour is asymmetric to the distal hub member lower contour about the distal horizontal axis, and the proximal hub member upper contour is asymmetric to the proximal hub member lower contour about the proximal horizontal axis. The distal hub member upper contour may align with the proximal hub member upper contour, and the distal hub member lower contour aligns with the proximal hub member lower contour.

While the invention has been described in connection with various embodiments, it will be understood that the invention is capable of further modifications. This application is intended to cover any variations, uses or adaptations of the invention following, in general, the principles of the invention, and including such departures from the present disclosure as, within the known and customary practice within the art to which the invention pertains.

What is claimed is:
1. A catheter hub apparatus comprising:
  a. a distal hub member coupled to a proximal end of a catheter sheath comprising
    i. a body member having an inside surface defining a longitudinal lumen, and
    ii. a proximal hub attachment member comprising a proximally-extending arm and a resilient projection;
  b. a proximal hub member fixedly coupled to a proximal end of a catheter comprising
    i. an outer wall defining an internal cavity and having an open distal end,
    ii. a central mounting section comprising a distally-extending annular wall defining a longitudinal lumen, an annular shelf, and an opening at a proximal end of the proximal hub member, and iii. a catch opening formed in the outer wall of the proximal hub member;

c. a core member disposed in the central mounting section of the proximal hub member, the core member comprising i. a wall defining a longitudinal lumen,
ii. a flange at a proximal end of the core member,
iii. an annular detent, and
iv. an annular recess;

d. a sealing member attached to the inside surface of the body member of the distal hub member, the sealing member comprising a wall defining a longitudinal lumen of the sealing member, the longitudinal lumen of the sealing member having a diameter greater than an outside diameter of the core member;

e. a hemostasis valve interfacing with the inside surface of the body member of the distal hub member and an annular shelf on a distal end of the sealing member; and f. an o-ring seated within the annular recess of the core member;

g. wherein the catheter fixedly coupled to the proximal hub member is disposed within the catheter sheath coupled to the distal hub member, the resilient projection is configured to engage with and at least partially pass through the catch opening to removably couple the distal hub member and the proximal hub member, the catheter is longitudinally movable within the sheath until the distal hub member is removably coupled to the proximal hub member, and the distal hub member disengages from the proximal hub member by disengaging the resilient projection from the catch opening and to longitudinally move the catheter and proximal hub member proximally away from the distal hub member, the hemostasis valve forms a fluid barrier preventing proximal fluid flow between a distal end of the longitudinal lumen of the distal hub member and the annular shelf on the distal end of the sealing member, and the o-ring forms a fluid barrier between a distal end of the longitudinal lumen of the sealing member and the internal cavity of the proximal hub member; the distal hub member further includes a side port in fluid communication with the longitudinal lumen of the distal hub member; and the wall of the core member comprises a first annular taper formed at the distal end of the core member and a second annular taper intermediate the annular recess and the flange at a proximal end of the core member; the longitudinal lumen of the sealing member includes a narrow distal section, a wide proximal section, a tapering intermediate section, and a tapering proximal section; the first annular taper of the core member interfaces with the tapering proximal section of the sealing member, such that the o-ring interfaces with the surface of the longitudinal lumen of the sealing member and creates the fluid barrier between the longitudinal lumen of the sealing member and the first annular taper of the core member; the sealing member is attached to the inside surface of the distal hub member by press fit or adhesives.

2. The catheter hub apparatus of claim 1, wherein the resilient projection deflects radially inward to pass through the open distal end of the proximal hub member.

3. The catheter hub apparatus of claim 2, wherein the resilient projection is biased radially outward and resiliently returns to its original position when engaged with the catch opening.

4. The catheter hub apparatus of claim 1, wherein the catch opening comprises an aperture in the outer wall of the proximal body member having a distal interfacing surface.

5. The catheter hub of claim 4, wherein the resilient projection has a tab configured to protrude through the aperture of the catch opening.

6. The catheter hub of claim 5, wherein the tab is a radially-extending tab of the resilient projection that includes an aperture in the protruding section of the radially-extending tab.

7. The catheter hub of claim 1, wherein the resilient projection is integrally formed with the distal hub member.

8. The catheter hub of claim 1, wherein the annular shelf of the central mounting section includes a flat proximal-facing surface on the proximal end of the central mounting section; and the flange at the proximal end of the core member engages with the proximal-facing surface of annular shelf.

9. The catheter hub of claim 8, wherein the hemostatis valve includes a distal valve member and a proximal valve member, wherein the proximal valve member defines a proximal surface and a radially outside surface; the longitudinal lumen of the distal hub member comprises a first expanded section configured to interface with the distal valve member preventing fluid flow therethrough and the proximal surface of the proximal valve member interfaces with the annular shelf of the sealing member.

10. The catheter hub of claim 9, wherein the longitudinal lumen of the distal hub member further comprises a second expanded section that includes a diameter larger than the first expanded section, wherein the radially outside surface of the proximal valve member attaches to the second expanded section.

11. The catheter hub of claim 10, wherein the longitudinal lumen further comprises a third expanded section configured to interface with the sealing member.

12. The catheter hub of claim 11, wherein the catheter is coaxially disposed and fixed within the longitudinal lumen of the core member.

13. The catheter hub of claim 1, wherein the longitudinal lumen of the core member comprises a distal section having a first diameter and a proximal section having a second diameter, wherein the second diameter is greater than the first diameter.

14. The catheter hub of claim 13, further comprising a UV-curable resin disposed within the proximal section of the longitudinal lumen of the core member, wherein the UV-curable resin has been cured with an application of UV radiation thereto.

15. The catheter hub of claim 14, wherein the wall of the core member is a UV-transparent material.

* * * * *